United States Patent [19]
Morales

[11] Patent Number: 5,810,815
[45] Date of Patent: Sep. 22, 1998

[54] SURGICAL APPARATUS FOR USE IN THE TREATMENT OF SPINAL DEFORMITIES

[76] Inventor: Jose A. Morales, Norte 62-A No. 5128 Dept #1, Distrito Federal Mexico 07869, Mexico

[21] Appl. No.: 716,895

[22] Filed: Sep. 20, 1996

[51] Int. Cl.$^6$ .................................................. A61B 17/58
[52] U.S. Cl. .............................................. 606/61; 606/60
[58] Field of Search ................................. 606/61, 60, 53, 606/62, 64, 69, 71, 74

[56] References Cited

U.S. PATENT DOCUMENTS

| | | | |
|---|---|---|---|
| 4,573,454 | 3/1986 | Hoffman | 606/61 |
| 4,686,970 | 8/1987 | Dove et al. | 606/61 |
| 5,102,412 | 4/1992 | Rogozinski | 606/61 |

*Primary Examiner*—Michael Buiz
*Assistant Examiner*—Julian W. Woo

[57] ABSTRACT

An apparatus for treating spinal vertebrae of patients that requires therapeutic mechanical effects. This apparatus permits a surgeon to readily adjust the overall dimensions of the apparatus and its structural members according to the needs of the patient by telescopically moving the upper and lower frame members with an adjustable connector. A supporting assembly rigidly mounts the apparatus to suitable parts of the patient's body and it is also flexible enough to adjust to the peculiarities of each patient by permitting the lower frame to be selectively mounted to the supporting assembly. Also, in areas where the apparatus cannot be secured through the supporting assembly to the sacrum bone, wires are used to secure it to the vertebrae.

7 Claims, 3 Drawing Sheets

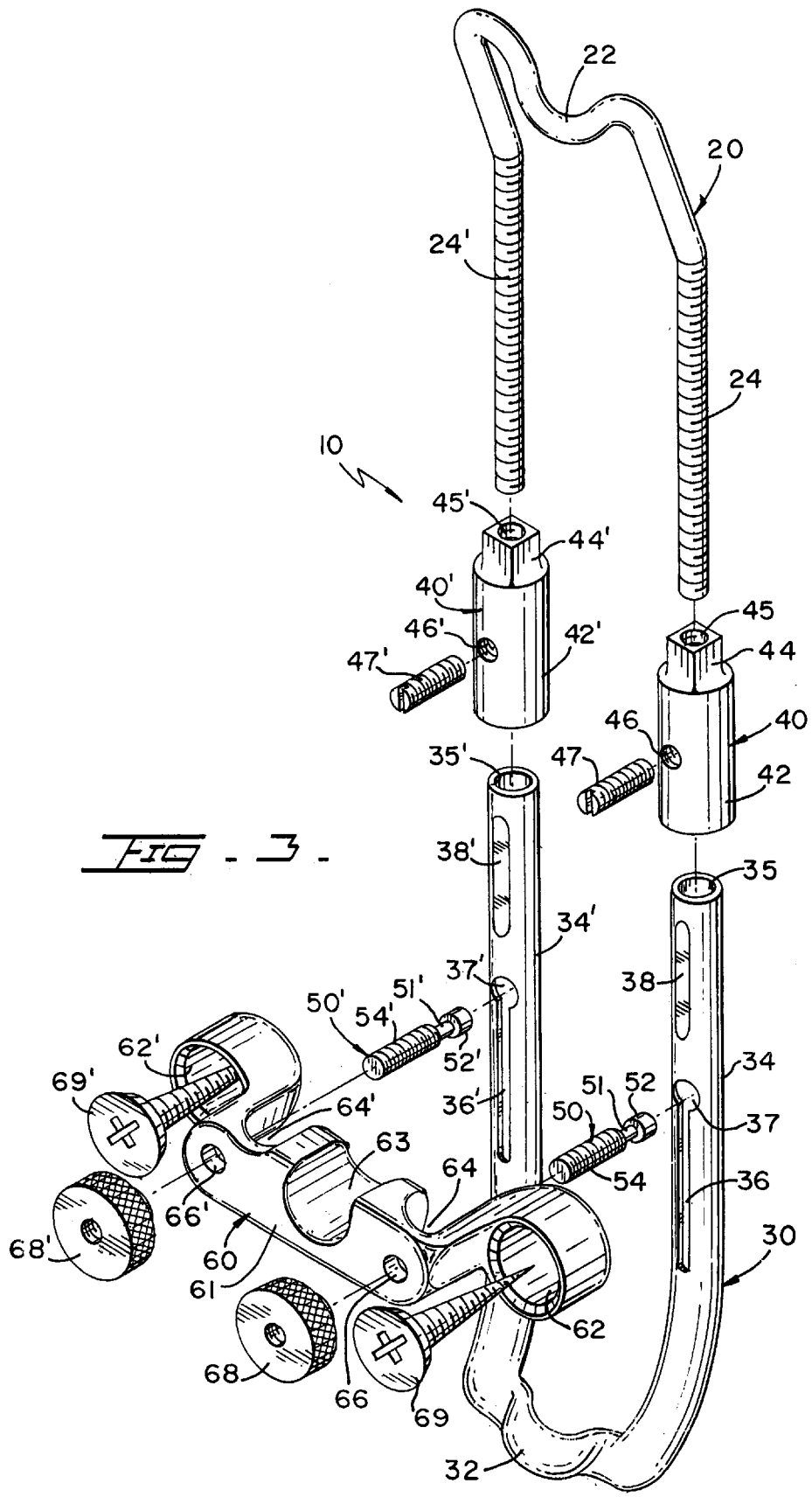

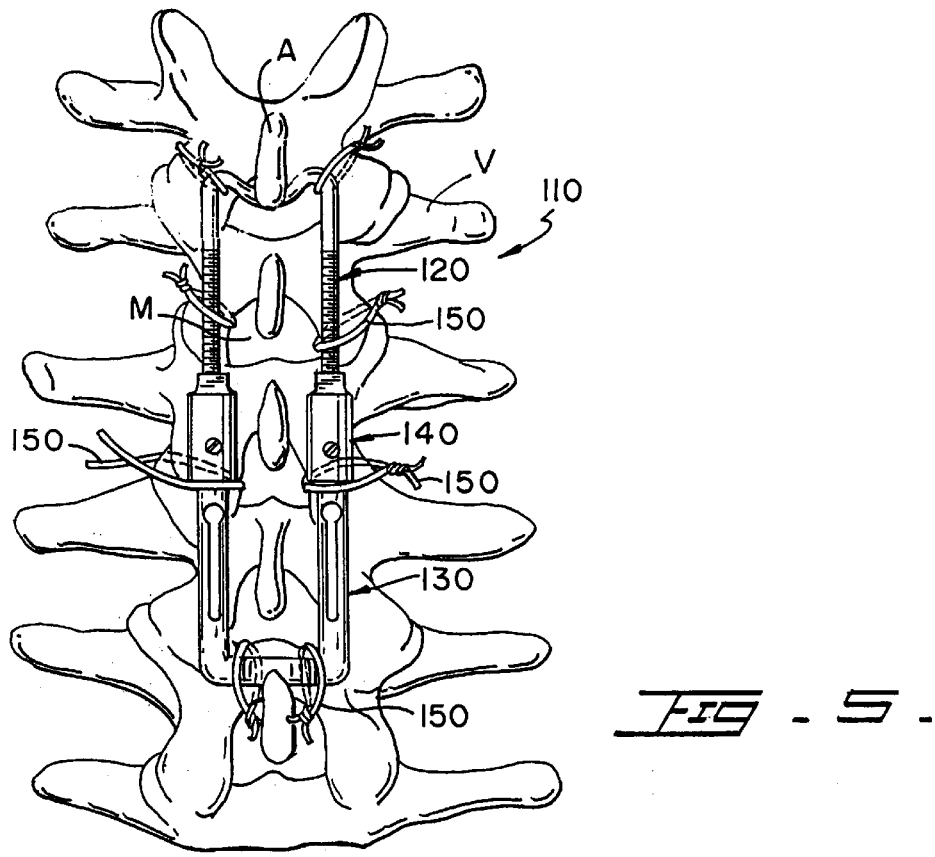
FIG - 5 -
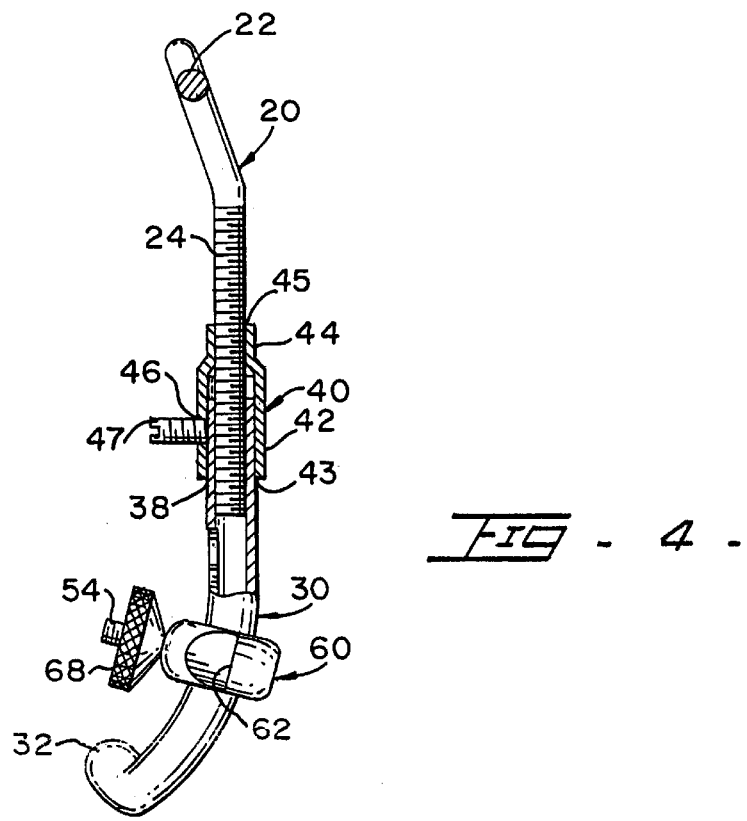
FIG - 4 -

SURGICAL APPARATUS FOR USE IN THE TREATMENT OF SPINAL DEFORMITIES

BACKGROUND OF THE INVENTION

1. Field of the Invention

The present invention relates to a surgical apparatus for use in the treatment of spinal deformities, such as an orthrodesis of lumbar, dorsal and/or the cervical portions, and/or inestability of any of the spine segments.

2. Description of the Related Art

Applicant believes that one of the closest reference corresponds to U.S. Pat. No. 5,102,412 issued to Rogozinski in 1992. However, it differs from the present invention in several materials aspects. First, the patented system requires molding of the bars 13 during the operation. The present invention utilizes two pre-formed bars that can be readily adapted to the anatomical features of the patient, with very fine adjustments possibilities by rotating connector assembly 40, as required. There are considerably more moving parts in Rogozinski's device, an undesirable feature, including transversal couplers 70 and shanks 42. The present invention also minimizes inventory requirements.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a device that can be used to promote anatomic alignment of the spine by immobilizing it until arthrodesis treatment is completed, restoring anatomical forms of the spine, spinal discs, as well as foraminal holes and to achieve the distraction or contraction of the spine, just as it was before the lesion.

It is another object of this invention to provide a device that is used for segmental fixation of the vertebrae in the spinal column.

It is still another object of the present invention to provide a device that has a telescopic feature that can be adapted to different sizes and deformities of a spinal column.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 3 is an exploded view of an isometric view showing the present invention.

FIG. 4 is an elevational side view of a partial cross section of this invention.

FIG. 5 is an elevational front view of the other variation of the present invention.

DETAILED DESCRIPTION OF THE PREFERRED EMBODIMENT

Figure 1:
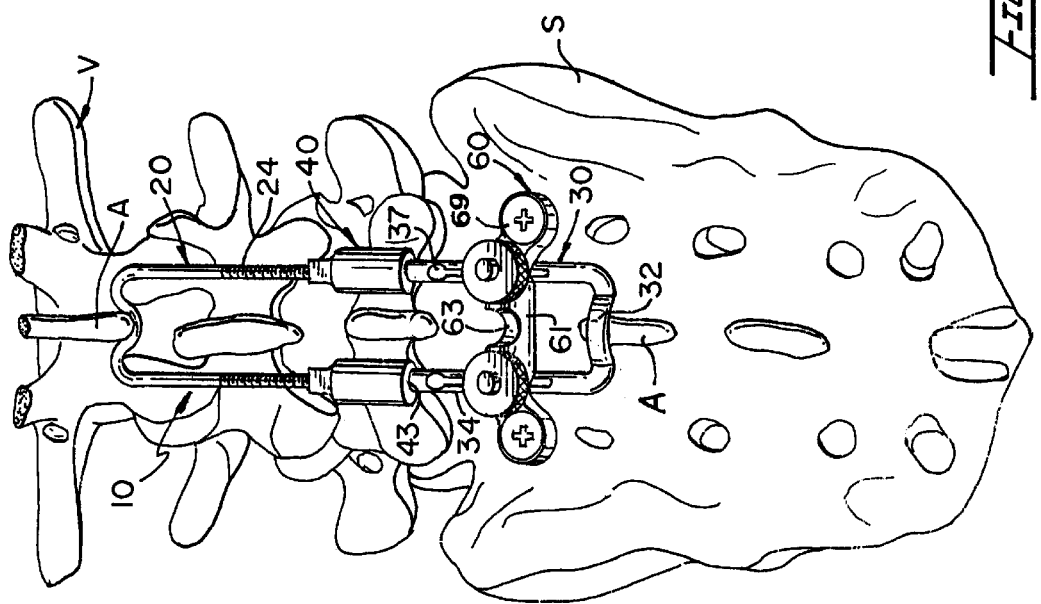
FIG. 1 is a front view of the present invention surgically mounted to the lumbar portion of a spinal column.
Figure 2:
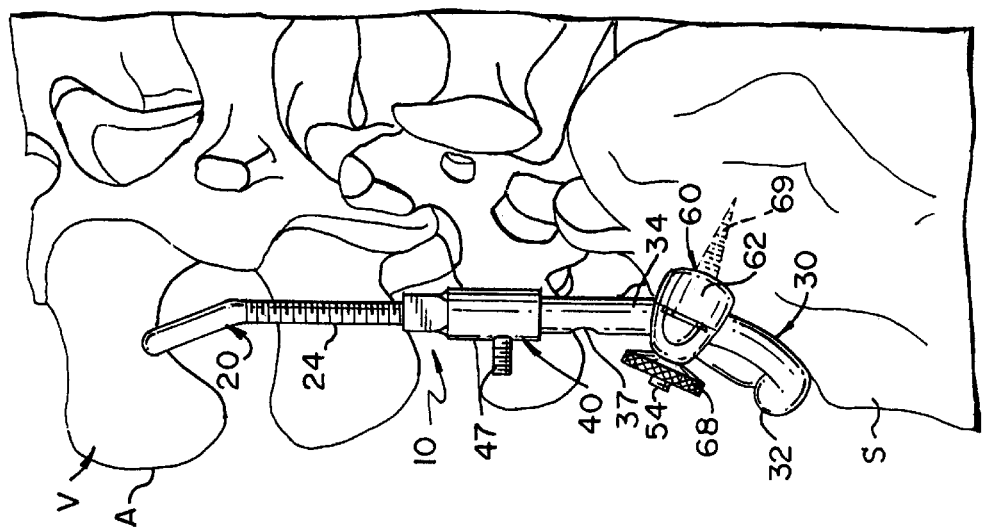
FIG. 2 is an elevational side view of this invention, shown in the previous figure.

Referring now to FIGS. 1 through 4, where the present invention is generally referred to with numeral 10, it can be observed that it basically includes lower and upper frames 20 and 30 interconnected to each other through connector assemblies 40 and 40'. Mounting assembly 60 affixes tool 10 to a body.

Upper frame 20, as shown in FIGS. 1 through 5, includes threaded bars 24 and 24', that are spaced apart and kept in parallel relationship to each other by arcuated spacer member 22. Threaded bars 24 and 24' are cooperatively received by threaded openings 45 and 45' of connector assemblies 40 and 40'.

Connector assemblies 40 and 40', in the preferred embodiment, include cylindrical tubular portions 42 and 42', and internally threaded portions 44 and 44' adjacent and collinearly disposed with respect to each other. Portions 44 and 44' have threaded openings 45 and 45', respectively, to cooperatively receive threaded bars 24 and 24' of upper frame 20. Cylindrical tubular portion 42 has a sufficiently large diameter for its centrally disposed opening 43 to permit threaded bars 24 and 24' to go through, as best seen in FIG. 4.

Lower frame 30, in the preferred embodiment in FIG. 3, has elongated tubular members 34 and 34' spaced apart and in parallel relationship by arcuated spacer member 32. The uppermost ends of elongated tubular members 34 and 34' of lower frame 30 include openings 35 and 35', as best seen in FIG. 4. Elongated tubular members 34 and 34' have slots 36 and 36', respectively, that are located in the central portion of elongated tubular members 34 and 34'. Slots 36 and 36' have enlarged ends 37 and 37', respectively, that are designed to allow through heads 52 and 52' of screws 50 and 50'. Necks 51 and 51' are allowed to slide down along slots 36 and 36'.

Frames 20 and 30 are kept in place and connected to each other through connector assemblies 40 and 40' that include set screws 47 and 47', respectively. Set screws 47 and 47' pass through openings 46 and 46', respectively, and are adjusted against flatten areas 38 and 38' located at the uppermost portion of lower frame 30.

As mentioned above, upper and lower frames 20 and 30 have arcuated spacer members 22 and 32 which are mainly ergonometrically designed to rest on spine apophysis A causing the distraction of the spinal column by adjusting frames 20 and 30, according to the medical needs.

Supporting assembly 60 mounts apparatus 10 to a patient's bone, such as sacrum bone S, for therapeutical treatment of the lumbar vertebrae of the spinal column. The present invention, when used in the lumbar area, can be used on all lumbar vertebrae and the sacrum bone. Supporting assembly 60 includes bar 61 with spaced apart eye members 62 and 62' through which screw members 69 and 69' pass, respectively, to affix assembly 60 to the sacrum bone. Bar 61 of supporting assembly 60 includes also bays 64 and 64' which cooperative embrace elongated tubular members 34 and 34'. Bays 64 and 64' have through openings 66 and 66', respectively, through which screws 50 and 50' pass. Screws 50 and 50' include heads 52 and 52' and threaded ends 54 and 54'. Heads 52 and 52' are inserted through enlarged ends 37 and 37' of tubular members 34 and 34', respectively. The position of assembly 60 is adjusted to the desired position by sliding head members 52 and 52' along slots 36 and 36', as best seen in FIG. 3. Once the desired position is achieved, assembly 60 is rigidly fastened to members 34 and 34' by screws 50 and 50' through openings 66 and 66' and then secured by nuts 68 and 68', respectively. Assembly 60 is then fastened to the patient's sacrum bone by screw members 69 and 69', as illustrated in FIGS. 1; 2 and 3. Apparatus 10 can be mounted to any of the fifth vertebrae located in the lumbar portion of the column and to the sacrum bone S. Bay 63 is ergonometrically designed to permit cooperative positioning of device 10 with minimum discomfort for the user.

When the therapeutical treatment needs to be applied to in the dorsal vertebrae and/or cervical vertebrae, supporting assembly 60 is substituted with wires 150, as shown in embodiment 110 in FIG. 5. Wires 150 are secured over the entire structure apparatus 110 and vertebrae V passing through medullar conducts M. Apparatus 110 includes upper and lower frames 120 and 130 and a structure very similar to as apparatus 10, described above. Connector assembly 140 adjusts and connects upper and lower frames 120 and 130 to be positioned around the affected area of a patient, in the same manner as assembly 60 connects members 20 and 30.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An apparatus for treating spinal vertebrae, comprising:
   A) an upper frame assembly having symmetrical first and second elongated members with first and second ends each, and a first spacer member rigidly connected to said first ends so that said first and second elongated members are kept in a parallel and spaced apart relationship with respect to each other;
   B) a lower frame assembly having symmetrical first and second tubular members with third and fourth ends each, and a second spacer member rigidly connected to said third ends, and said fourth ends having each a centrally and longitudinally extending opening of cooperative dimensions to receive said second ends;
   C) connector means for telescopically adjusting the position of said first and second elongated members within said first and second tubular members; and
   D) means for mounting said apparatus to the bones of a patient so that the desired mechanical support and distention can be selectively and gradually applied to predetermined vertebrae as deemed necessary by the operating surgeon.

2. The apparatus set forth in claim 1 wherein said connector means includes first and second connector members, including each fifth and sixth ends, and said first and second connector members releasably locking said second ends and said fourth ends in place relative to each other thereby permitting a user to vary the overall length of said apparatus to achieve the required mechanical result.

3. The apparatus set forth in claim 2 wherein said first and second connectors members have each a longitudinally extending through opening and an internal thread adjacent to said fifth ends and said through opening having a larger diameter in the portion adjacent to said sixth ends, and said second ends include each an outer thread that cooperatively engages with said internal thread to cause said connector members to advance along coaxially along said firs and second elongated members.

4. The apparatus set forth in claim 3 wherein said means for mounting said apparatus includes a bar having two ends defining eyelets and first fastening means for rigidly mounting said apparatus to a user's sacrum bones.

5. The apparatus set forth in claim 4 wherein said bar includes first and second bays for cooperatively partially embracing said first and second tubular members and second fastening means for securely mounting said means for mounting said apparatus to said first and second tubular members.

6. The apparatus set forth in claim 5 wherein said first and second tubular members include each a longitudinally extending slot with an enlarged end and said second fastening means include two headed screws so that said means for mounting said apparatus can be selectively mounted at different positions along said slots.

7. The apparatus set forth in claim 1 wherein said means for mounting said apparatus includes a wire member.

\* \* \* \* \*